(12) United States Patent
Smith

(10) Patent No.: US 7,032,322 B1
(45) Date of Patent: Apr. 25, 2006

(54) METHOD FOR PROCESSING INFECTIOUS WASTE AND SYSTEM FOR THE SAME

(75) Inventor: Donald L. Smith, Greenville, SC (US)

(73) Assignee: Sterassure Solutions, L.L.C., Greenville, SC (US)

( * ) Notice: Subject to any disclaimer, the term of this patent is extended or adjusted under 35 U.S.C. 154(b) by 0 days.

(21) Appl. No.: 10/981,138

(22) Filed: Nov. 4, 2004

(51) Int. Cl.
*F26B 21/06* (2006.01)

(52) U.S. Cl. ............................................ 34/77; 241/22

(58) Field of Classification Search .................... 34/77, 34/80, 90; 241/20, 33; 422/21, 26
See application file for complete search history.

(56) References Cited

U.S. PATENT DOCUMENTS

| | | | | |
|---|---|---|---|---|
| 2,942,877 | A | * | 6/1960 | Fowlie et al. .................. 271/31 |
| 4,282,105 | A | * | 8/1981 | Crowe ........................ 210/798 |
| 5,192,131 | A | | 3/1993 | Hatfield |
| 5,277,869 | A | | 1/1994 | Glazer et al. |
| 5,427,737 | A | | 6/1995 | Glazer et al. |
| 5,566,890 | A | * | 10/1996 | Ricciardelli .................. 241/20 |
| 5,582,793 | A | | 12/1996 | Glazer et al. |
| 5,666,878 | A | | 9/1997 | Taricco |
| 5,709,234 | A | * | 1/1998 | Lashmett et al. ............. 134/92 |
| 5,741,238 | A | | 4/1998 | Bradbury et al. |
| 5,759,491 | A | | 6/1998 | Bunin |
| 5,776,118 | A | | 7/1998 | Seifert et al. |
| 5,837,171 | A | | 11/1998 | Danzik et al. |
| 5,885,001 | A | | 3/1999 | Thomas |
| 5,885,240 | A | | 3/1999 | Bradbury et al. |
| 5,915,636 | A | | 6/1999 | Caballero |
| 5,941,468 | A | | 8/1999 | Lewis et al. |
| 5,972,291 | A | | 10/1999 | Healy et al. |
| 6,039,724 | A | | 3/2000 | Seifert et al. |
| 6,076,958 | A | | 6/2000 | Althouse, III et al. |
| 6,079,314 | A | * | 6/2000 | Mackinnon ............... 99/289 R |
| 6,113,854 | A | | 9/2000 | Milum et al. |
| 6,139,793 | A | * | 10/2000 | Vanderwal ..................... 422/1 |

* cited by examiner

*Primary Examiner*—S. Gravini
(74) *Attorney, Agent, or Firm*—Dority & Manning, P.A.

(57) ABSTRACT

A processor and method for treating infectious waste utilizes a processing chamber having an inlet for delivering processing water at an elevated temperature and under pressure into the processing chamber, an opening in the processing chamber for receiving of infectious waste and for removing treated waste, an agitator for opening the waste material to the action of the water at elevated temperature and pressure. A basket and/or a sieve may be carried in the processing chamber to facilitate drainage of spent processing water, and an apparatus may be included for removing neutralized waste through the opening in the processing chamber either by inverting the processor or by removing and inverting the basket and/or sieve.

31 Claims, 12 Drawing Sheets

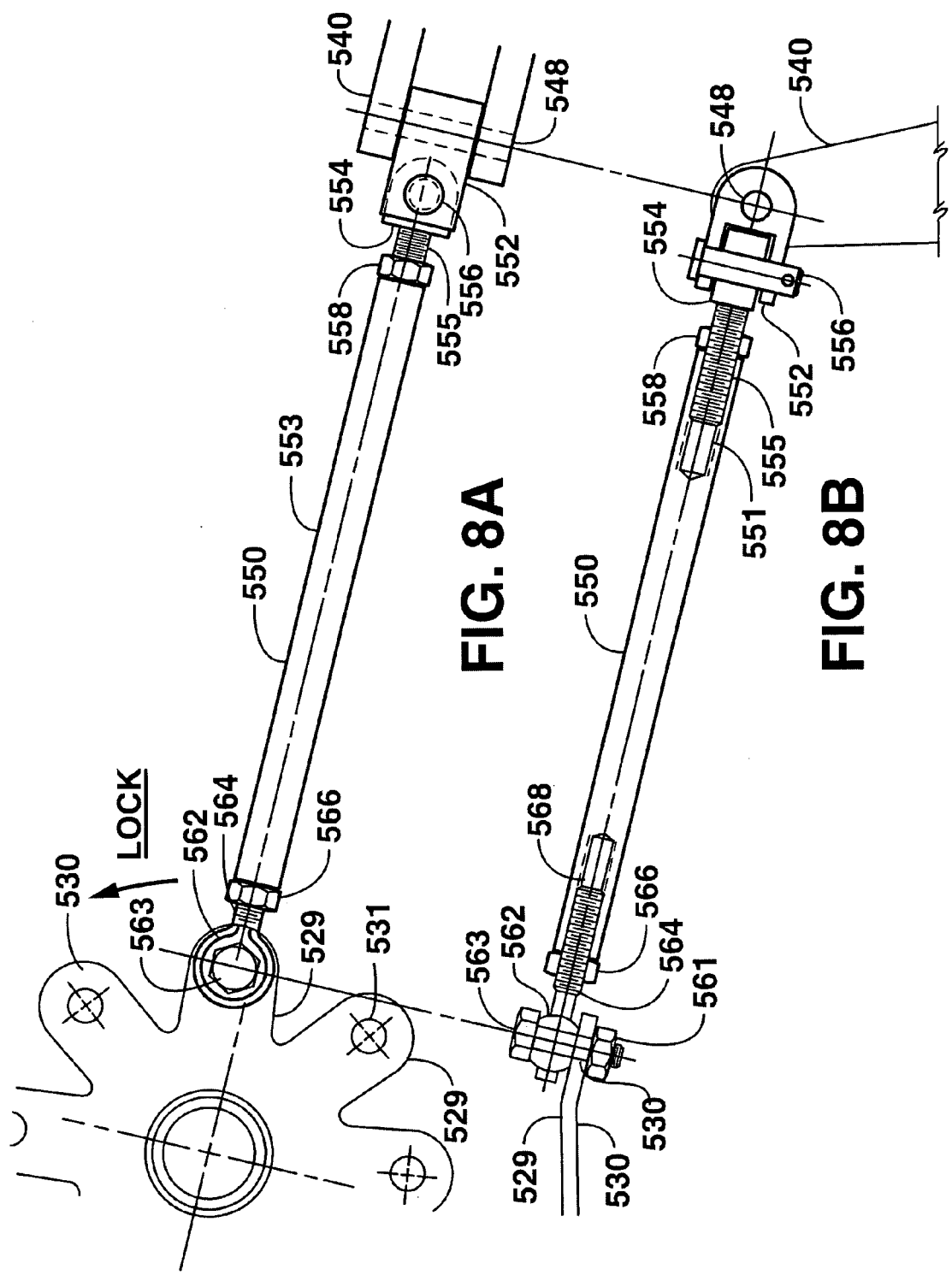

METHOD FOR PROCESSING INFECTIOUS WASTE AND SYSTEM FOR THE SAME

TECHNICAL FIELD OF THE INVENTION

This invention relates to a method useful for treating infectious waste as well as a system and processing apparatuses for carrying out the method.

BACKGROUND OF THE INVENTION

Currently, medical and biological waste, generally referred to herein as "infectious waste," generated in hospitals and other medical and research related facilities that contain disease-producing organisms or pathological wastes may be disposed through several disposal processes such as steam sterilization, microwave or plasma radiation, or incineration. These processes often require large expensive equipment and can pose environmental problems.

Systems for using hot liquids to sterilize the infectious waste have also been developed. These systems employ large tanks wherein a pump for chopping and circulating the waste material through the system circuit is contained within the system. These systems required large quantities of fresh liquid that require a long period of time to heat to the desired processing temperature. Further, once the liquid is used to process the infectious waste, the liquid is disposed of. Before the system can be used again, the user must wait for the next batch of fresh process liquid to heated to the desired temperature. Such use of large quantities of liquid is costly not only in the use of the large quantity of liquid, but also through the large expenditure of energy needed to heat each batch of the liquid to the desired temperature.

Another concern with these hot liquid systems is that the pumps used within the systems are industrial pumps having ridge blades that pulverize waste. The pumps are prone to clogging by flexible waste such as tubing and textile waste that wraps around the blades and are subject to damage by metal objects such as clamps, scalpel blade holders. Therefore, the pumps must be cleaned on a regular basis. Due to the construction of the system, these pumps are hard to access and clean. Further, when the pump inevitably fails, repair is difficult and dangerous because the pump and system are clogged with infectious waste. Further, due to the massive size of these systems it is nearly impossible to remove the system for off-site repair.

Therefore, a need exists for a process and system for treating infectious waste that can increase the efficiency and safety of treating the waste.

SUMMARY OF THE INVENTION

The present subject matter recognizes and addresses the above briefly discussed drawbacks, and others of above-described processes and systems for treating infectious waste. Accordingly, a general aspect of the present subject matter is to provide a process and a system, as well as different components of the system, that can increase the efficiency and safety of treating infectious waste. Additional aspects and advantages of the invention will be set forth in part in the following description, or may be obvious from the description, or may be learned through practice of the invention.

In an exemplary embodiment, a method for processing infectious waste is provided. Heated water is introduced under pressure into a processing chamber that contains infectious waste. The heated water should be at a temperature that biologically neutralizes the infectious waste. The infectious waste and the heated water are agitated through the action of an agitator to a point where the infectious waste is neutralized by the heated water. The temperature of the water is maintained at a temperature that biologically neutralizes the infectious waste at least until such neutralization occurs.

The water is then forced from the processing chamber by a pressure differential. During the removal of the water, the water forced from the processing chamber is strained to keep the waste material within the processing chamber. As the water is removed, at least a portion of the water is recycled to be reused in processing further infectious waste. The neutralized waste is then cooled within the processing chamber before being removed from the processing chamber.

To perform the above-described method, an exemplary embodiment of a system for processing infectious waste to neutralize the waste is provided. The system includes a processing chamber for receiving infectious waste and processing water that is at an elevated temperature sufficient to process said infectious waste. The processing chamber defines an opening through which to receive and remove the waste. A closure member is carried adjacent to the processing chamber. The closure member is positionable over the opening defined in the processing chamber so as to seal the processing chamber closed. Further, the closure member is removable from the opening of the processing chamber to permit receipt of the waste before processing and removal of the waste after the waste has been neutralized.

A holding tank is connected to the processing chamber. The holding tank supplies the processing water at the elevated temperature sufficient to process the infectious waste in the processing chamber. A filter is disposed between the processing chamber and the holding tank. The filter cleans the processing water that exits the processing chamber and supplies at least a portion of the filtered processing water back to the holding tank to be reused in the processing chamber. In this manner, water can be recycled increasing the efficiency of the processing system.

An exemplary embodiment of an apparatus for use in a system for processing infectious waste is also provided. The apparatus includes a processing chamber for receiving infectious waste and processing water that is at an elevated temperature sufficient to process the infectious waste. The processing chamber forms an opening through which to receive and remove the waste. A closure member is carried adjacent to said processing chamber. The closure member is positionable over the opening formed in the processing chamber so as to seal the processing chamber closed. Further, the closure member is removable from the opening of the processing chamber to permit receipt of the waste for processing and removal of the waste after said waste has been neutralized.

An agitator extends within the processing chamber. The agitator has a rotatable internal shaft possessing an axis extending through the process chamber with a tapered blade carrier disposed on a free end of the shaft. A plurality of blades are pivoted about pivot points on the tapered blade carrier. The blades are spring-loaded and are biased upward parallel to the axis of the internal shaft at rest. Upon rotation of the shaft, centrifugal force causes the blades to extend outward from the blade carrier about the pivot points into an angular position as measured from the axis of the internal shaft. The agitator spins the blades within the processing chamber when the processing chamber is filled with heated water and infectious waste, thereby mixing the heated water and infectious waste thoroughly to biologically neutralize the infectious waste by rapidly exposing the waste to the heat in the water.

An exemplary embodiment of a pressure sealable chamber closure member which is usable in the processing apparatus includes a lid with a rotatable hub located on the lid. A plurality of latch arms is connected to the hub on first ends of the latch arms. The hub is rotatable in a first direction so that the latch arms rotate causing a second end of each of the latch arms to latch the lid onto the processing chamber. When the hub is rotated in a second direction, the latch arms rotate causing the second end of each of the latch arms to unlatch the lid from the processing chamber.

Within the processing chamber, an exemplary embodiment of a centrifugal agitator may include a rotatable internal shaft having a first end and a second end with an axis that extends vertically therethrough. A rotatable blade carrier is mounted on the first end of the shaft. The blade carrier has a surface tapering inwardly toward a free end of the blade carrier.

A plurality of blades is pivotally connectable to the tapered blade carrier with the blades being spaced about the free end of the blade carrier. Springs are carried by the blade carrier and in communication with the blades and the blade carrier. The springs bias the blades upward about parallel to the axis of the internal shaft when the blades are in a resting position. The blades are then extendable upon rotation of the shaft to outward positions from the blade carrier about the pivot points as measured from the axis of the internal shaft due to centrifugal force. In this manner, the blades can interact with the processing water and waste without becoming immobilized by the waste.

All the features of the subject matter will be described in greater detail through the use of the appended figures.

BRIEF DESCRIPTION OF THE DRAWINGS

A full and enabling disclosure of the present invention, including the best mode thereof, to one of ordinary skill in the art is set forth more particularly in the remainder of the specification, including reference to the accompanying figures, in which:

FIG. 8A is a top view illustrating a hub and connecting arm of the chamber closure member of FIG. 7;

FIG. 8B is a cross-sectional view illustrating the hub and connecting arm of FIG. 8A;

DESCRIPTION OF THE PREFERRED EMBODIMENT

Reference will now be made in detail to the presently preferred embodiments of the invention, one or more examples of which are shown in the figures. Each example is provided to explain the invention, and not as a limitation of the invention. In fact, features illustrated or described as part of one embodiment can be used with another embodiment to yield still a further embodiment. It is intended that the present invention cover such modifications and variations.

Figures 1, 11B:
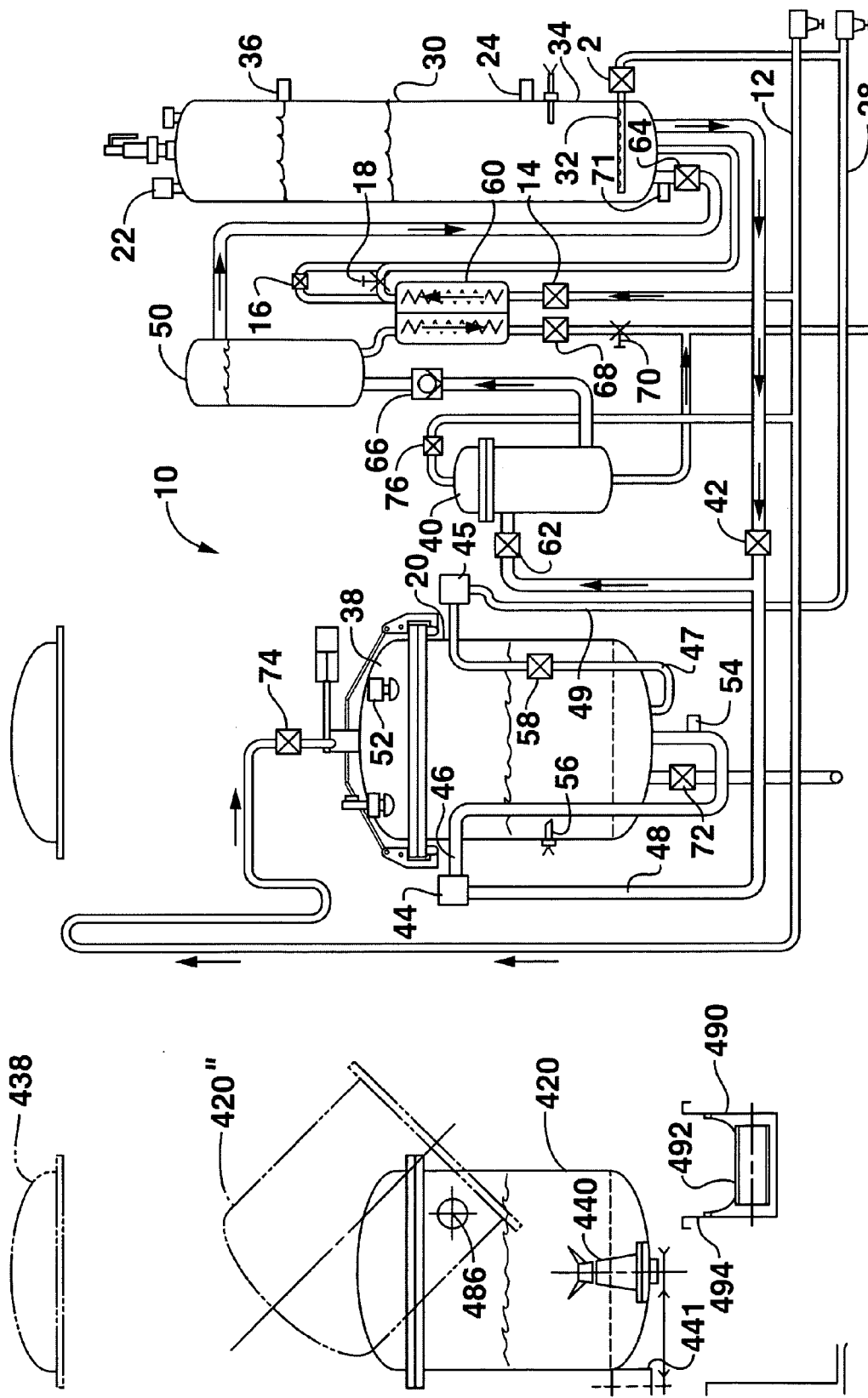
FIG. 1 is a schematic view illustrating an exemplary embodiment of a system for processing infectious waste in accordance with the present invention.
FIG. 11B is another schematic side view illustrating the processing chamber and removal apparatus shown in FIG. 11A.

FIG. 1 illustrates a system, generally 10, for processing infectious waste to biologically neutralize the waste so that the waste may be safely discarded or recycled. The system 10 includes a processing chamber 20, a holding tank 30, a filter 40, a transfer tank 50 and a heat exchanger 60 that are used to neutralize infectious waste using superheated water, while recycling at least a portion of the water to be reused again in the process. Thereby, efficiency of the processing of infectious waste can be increased and a savings in cost can be realized through the recycling of the heated water.

In general, the infectious waste is placed into the processing chamber 20 and a closure member 38, such as a lid, closes the processing chamber 20. The holding tank 30 supplies superheated process water to the processing chamber 20 to sterilize, or neutralize, the infectious waste contained therein. Once the waste has been neutralized, the process water is run through a filter 40 into a transfer tank 50. At least a portion of the filtered process water passes through transfer tank 50 and back into the holding tank 30. The rest of the process water remains in the transfer tank 50 and is run through the heat exchanger 60 to transfer heat from the process water to new water being supplied to the holding tank 30. The holding tank 50 is used to reheat the process water to a desired temperature for use in processing the next batch of infectious waste. A control and/or monitoring unit can be employed to control the system 10.

Before the system 10 can be used, water has to be introduced into the holding tank 30. The water can be regular tap water supplied by a municipality. To initialize the system, a valve 14 opens to allow water from a supply of water 12 to flow through the heat exchanger 60 and into the holding tank 30. Valve 16 opens to bypass the flow control valve 18 allowing a faster fill time. A vent valve 22 on top of the holding tank 30 opens to permit air to escape the holding tank 30 as the holding tank 30 fills. The size of the holding tank 30 may vary depending on the amount of waste to be processed which can be used to determine the amount of water needed to neutralize the waste and, in turn, designate the size of the processing chamber 20. For example, the holding tank 30 may be a 60-gallon tank.

When the level of water in the holding tank 30 reaches a first specified amount, a lower level sensor 24 activates a valve 26, causing the valve 26 to open, allowing steam from a supply of steam 28 to enter a sparge pipe 32, thereby heating the water as it enters the holding tank 30. For a sixty-gallon holding tank, the first specified amount at which the lower level sensor 24 activates the valve 26 may be twenty gallons. Water continues to flow into the 60-gallon tank until the upper sensor is reached. An upper level sensor 36 is set at a second specified amount of water. When the second specified amount of water has filled the holding tank 30 and the upper level sensor 36 is reached, valve 14 and valve 16 are activated stopping the water flow. For a sixty-gallon holding tank, the second specified amount of water at which the upper level sensor activates the valve 14 and 16 to stop the water flow may be fifty gallons.

A thermocouple 34 in the holding tank 30 monitors the water temperature. Valve 26 stays open allowing steam to continue to heat the water and vent valve 22 on the holding tank 30 stays open until the water temperature reaches approximately 212° F. for about a minute. This allows all of the air to escape the holding tank 30 and the remainder of the holding tank 30 is filled with steam. Valve 22 then closes and valve J stays open until the water reaches a desired temperature as the pressure in the holding tank 30 builds. Once the temperature reaches the desired level, the valve 26 closes. Valve 26 will reopen if the temperature falls below the desired level. The temperature should be high enough to neutralize the infectious waste. For example, a temperature of approximately 285° F. will more the adequately suffice. Steam pressure at 285 degrees F. is approximately 40 psig.

Once the holding tank 30 is filled to the desired level and the water is raised to the proper temperature, the processing of waste can begin. Waste is loaded into the processing chamber 20 and the closure member 38 is closed. When the closure member 38 on the processing chamber 20 is closed and locked, valve 42 opens allowing water to flow from the holding tank 30 into the processing chamber 20. The pressure in the holding tank 30 is greater than the pressure in the processing chamber 20, so the water flows with a great deal of force. Valve 52 opens allowing air to escape the processing chamber 20 as the water flows from the holding tank 30 into the processing chamber 20.

A flow sensor 54 located at the bottom of the processing chamber 20 where the water flows into the chamber 20 senses that the flow of water stops after the second specified amount of water has entered the processing chamber 20. The flow sensor 54 then activates valves 42 and 52 causing the valves 42 and 52 to close. As the water enters the processing chamber 20, it heats the processing chamber 20 and the waste in the processing chamber 20 by giving up some of its energy to the chamber 20 and the waste.

The temperature of the water will drop along with the pressure within the processing chamber 20. A thermocouple 56 monitors the temperature within the processing chamber 20. If the temperature drops below a specified level, then valve 58 opens allowing steam to sparge into the processing chamber 20 Thereby raising the pressure within the processing chamber 20 and raising the temperature back up to the desired processing temperature.

For example, the temperature of the water may drop from 285° F. to approximately 255° F. and the pressure will drop to approximately 18 psig. If the temperature drops below 255°, then valve 58 opens allowing steam to sparge into the processing chamber raising the temperature back up to the desired processing temperature of 255° F. to 256° F.

Shortly after the water has entered the processing chamber 20, an agitator located in the bottom of the processing chamber 20 starts to spin. The agitator causes the superheated process water to mix with the infectious waste by opening bags in which the infectious waste is contained and facilitating the exposure of the waste to the superheated water. The temperature of the water thereby biologically neutralizes the waste.

The waste should be exposed to the process water for a period of time long enough to neutralize the waste. At temperatures above 255° F., the processing time is approximately 10 minutes. When the necessary time has elapsed, the agitator stops, and the valves 62 and 64 open. Due to the pressure differential, the water then flows through the filter 40 and the transfer tank 50 back into the holding tank 60. At this time, the holding tank 60 is empty and has cooled sufficiently so that the pressure is at or near zero. The vent valve 22 can be opened to assure zero pressure. The 18 psig in the processing chamber 20 forces the water back into the holding tank 30.

A flow sensor 78 near the bottom of the holding tank 30 senses when the flow of water stops and closes valves 62 and 64. A portion of the water is retained in the transfer tank 50. A check valve 66 at the entry of the transfer tank 50 prevents the back flow of water out of the transfer tank 50. In this manner, only a part of the original process water is recycled back in the holding tank 30. For example, when the system uses fifty gallons of process water, only forty gallons of the original 50 gallons of water is returned to a 60-gallon holding tank.

Valve 14 opens allowing water from a supply of water 12 to flow through the heat exchanger 60 and into the holding tank 30. A flow control valve 18 controls the flow of water from the supply of water 12 through the heat exchanger 60. Normally, water from a municipality will flow at a rate of approximately two gallons per minute. Therefore, in an embodiment where ten gallons of water needs to be added to reach fifty gallons in the sixty-gallon tank, the water will be replenished in five minutes.

At the same time valve 14 opens, valve 68 also opens allowing the water in the transfer tank 50 to flow through the opposite side of the heat exchanger 60. Valve 70 controls the rate at which this water flows to approximately two gallons per minute for 5 minutes. The heat exchanger 60 is sized to remove a portion of the energy from the used water and return it to the fresh water as it flows into the holding tank 30. At the same time that valves 14 and 68 open, valve 26 opens to permit steam to sparge into the holding tank 30 in order to bring the water in that holding tank 30 back up to the desired level. In the embodiment using a sixty gallon holding tank, this process takes approximately 10 minutes.

Also, when valves 62 and 64 close, valve 74 opens momentarily to allow water from the supply of water 12 to spray from the top of the closure member 38 inside the processing chamber 20 in order to cool the waste inside the chamber 20. At the same time, valve 72 at the base of the processing chamber opens to drain the water sprayed from valve 74 into the processing chamber 20. When the waste has been cooled by the spray from the top of the processing chamber 20, valve 74 closes. The cooling water flows through valve 72 to drain. When the cooling water has drained and the waste is cooled, the closure member 38 on the processing chamber 20 unlocks and the closure member 38 rises to its open position. At that time, the waste is removed from the processing chamber 20. After the waste has been removed, the processing chamber 20 is ready to start the next processing cycle.

By recycling and reusing the process water, water consumption is kept to a minimum. Reclaiming a large portion of energy from the process water that is drained and not recycled makes for an energy efficient system. At the same time, adding fresh water with each cycle keeps the process water from becoming fouled. The entire system 10 can be drained periodically and refilled to ensure the quality of the process water being used. To ensure the effectiveness of the filter 40, the filter 40 may be cleaned periodically by back flushing the filter with a momentary burst of water by opening valve 76.

The systems 10 for processing infectious waste constructed in accordance with the invention are preferably controlled and monitored by a control system, such as conventional programmable logic controllers ("PLC"), such as suitable PLC's manufactured by Allen-Bradley, a division of Rockwell Automation based out of Milwaukee, Wis., central processing units ("CPU"), microcomputers, and the like. Through an appropriate set-up of the control system, the valves, agitators and/or closure members can be monitored and controlled separately or in communication with one another. Any conventional suitable control system or systems may be employed.

Figure 2:
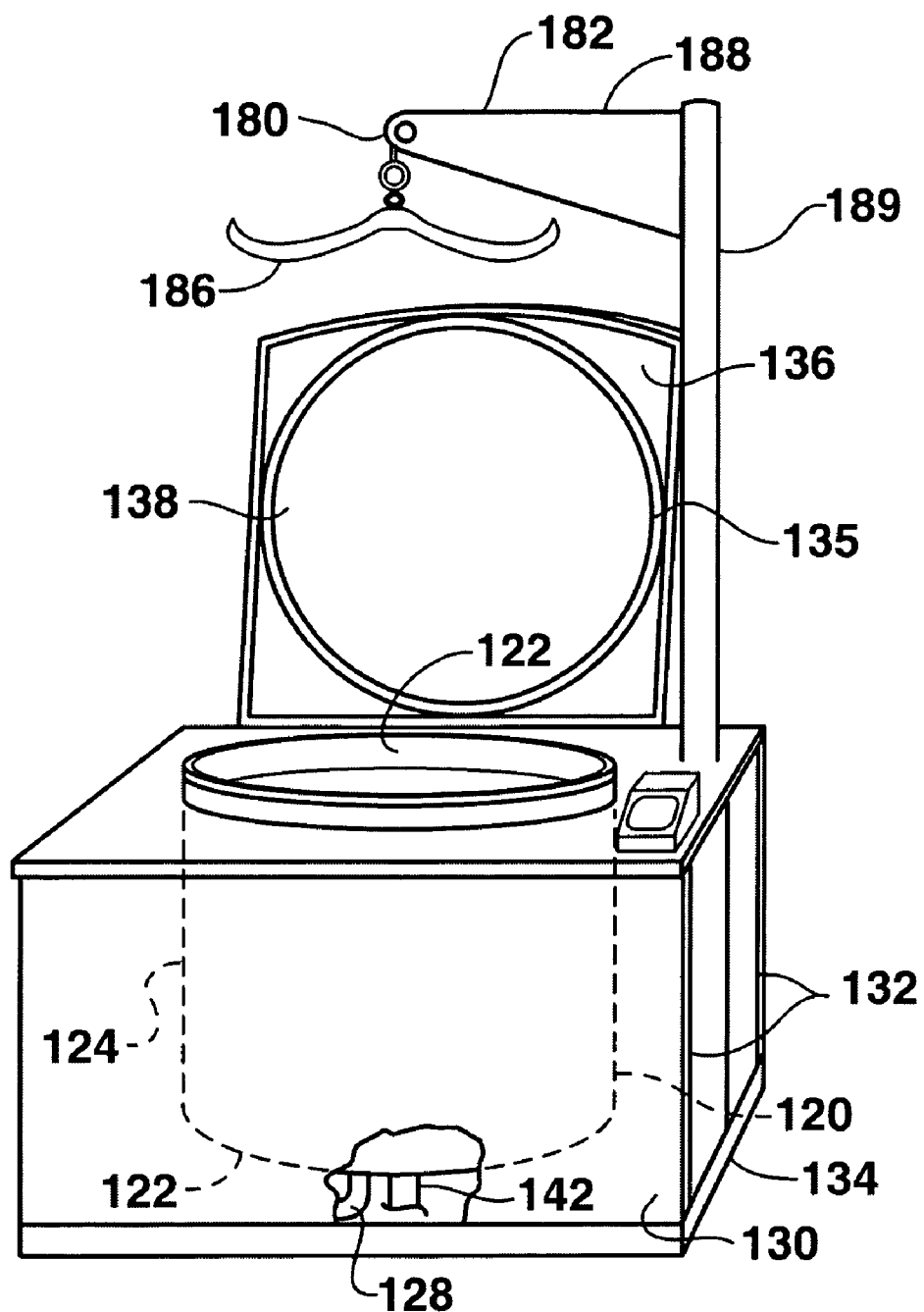
FIG. 2 is a front perspective view illustrating an exemplary embodiment of an apparatus for processing infectious waste constructed in accordance with the present invention.
Figure 3:
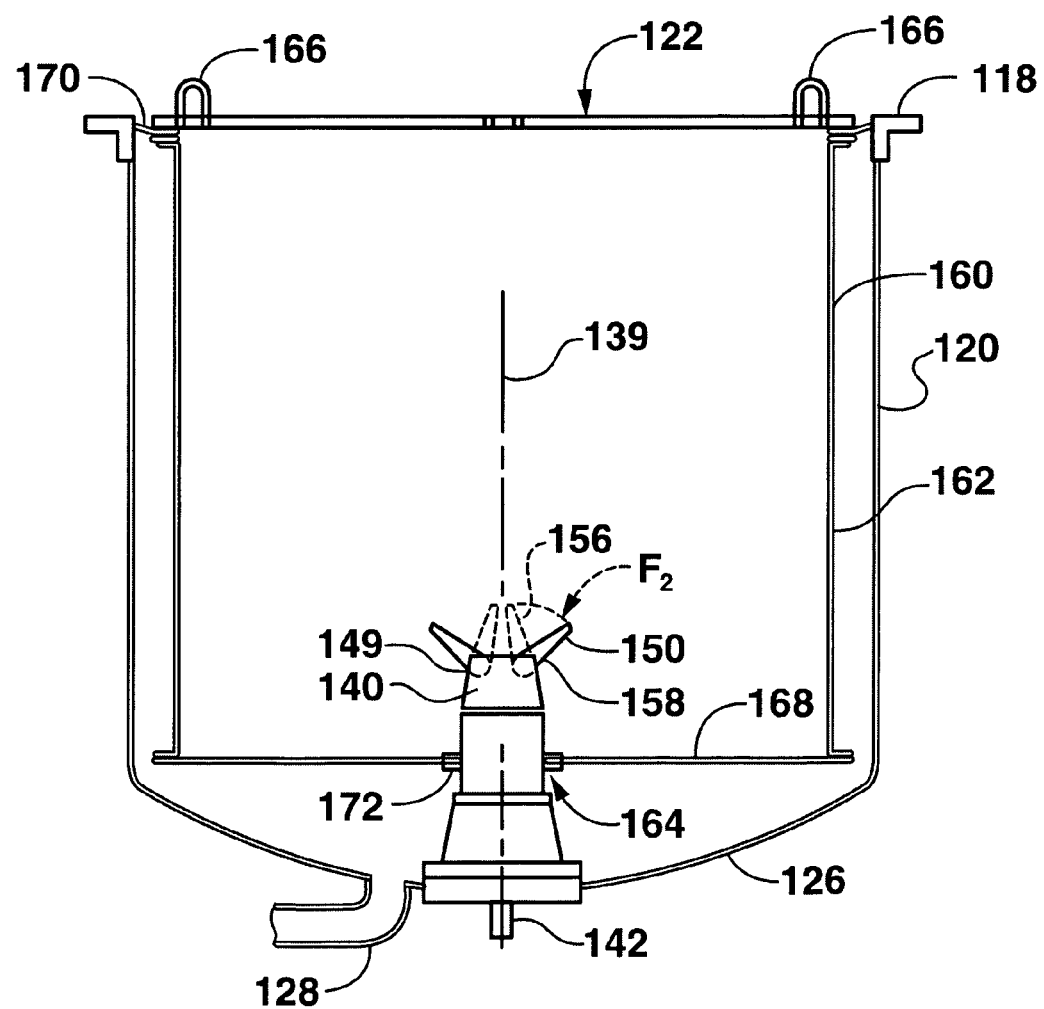
FIG. 3 is a cross-sectional view of the processing chamber shown in FIG. 2.

FIGS. 2 through 11 illustrate different exemplary embodiments of the processing chambers and related components. In FIGS. 2 and 3, a processing chamber 120 that can be used in the exemplary system described above is provided for treating infectious waste. The processing chamber 120 includes walls 124 and a concave bottom 126. At a top portion of the processing chamber 120, an opening 122 is defined by the walls 124. The opening 122 provides unobstructed access to the processing chamber 120 permitting loading of the infectious waste to be neutralized into the processing chamber 120.

The processing chamber 120 has a suitable housing 130 having a base 134 and access doors 132. The housing 130 provides an insulative barrier around the processing chamber 120 to prevent injury to operators due to the temperatures the exterior of processing chamber 120 can reach. The access doors 132 provide access to the processing chamber 120 and other various components to allow activities such as maintenance to be performed. The housing 130 can be easily disassembled for major overhauls.

A closure member, or lid, 138 is provided adjacent to the processing chamber 120 to sealably cover the opening 122 of the processing chamber 120. The closure member 138 has a cover top 136 disposed thereon to serve as a cover for the housing 130. The cover top 136 protects the operator from exposure to the temperatures which the closure member 138 can reach. The closure member 138 have seals along its rim 135 that hermetically seal the processing chamber 120 and closure member 138 when the pressure builds in the processing chamber from the superheated process water.

As can be seen from the cut away at the bottom of the housing 130, a line 128 is operably attached to the processing chamber 120 for providing the heated water from a holding tank in the system. The line 128 delivers heated water to the processing chamber 120 and thereafter drains the used water from the processing chamber 120. An internal shaft 142 of an agitator 140 extends upward through the bottom 126 of the processing chamber 120. The internal shaft 142 can be driven by a drive unit to spin the agitator 140 to thoroughly mix the process water supplied by line 126 with the infectious waste, thereby neutralizing the waste.

FIG. 3 shows a cross-sectional view of the processing chamber to better illustrate the relationship of the agitator 140 to the processing chamber 120. The agitator 140 of this exemplary embodiment is a centrifugal agitator that is located in the bottom 126 of the processing chamber 120 below a water line that the process water will reach when processing the infectious waste. An axis 139 of the agitator is in line with the axis of the processing chamber 120. The agitator 140 has a plurality of blades 150 disposed on a free end 149 of the agitator 140. As the internal shaft 142 is rotated, the blades 150 are extended by centrifugal force in a direction $F_2$ from a resting position 156 to an extended position 158. The process water within the processing chamber 120 is stirred up by the rotating agitator blades 150 along with the waste that has been placed in the processing chamber 120.

The placement of the agitator within the processing chamber is not critical, as long as it allows for proper circulation of the heated water and allows for removal of the waste from the processing chamber. Further, multiple agitators can be employed within a processing chamber to increase the circulation of the waste and heated water in some embodiments.

Figure 5:
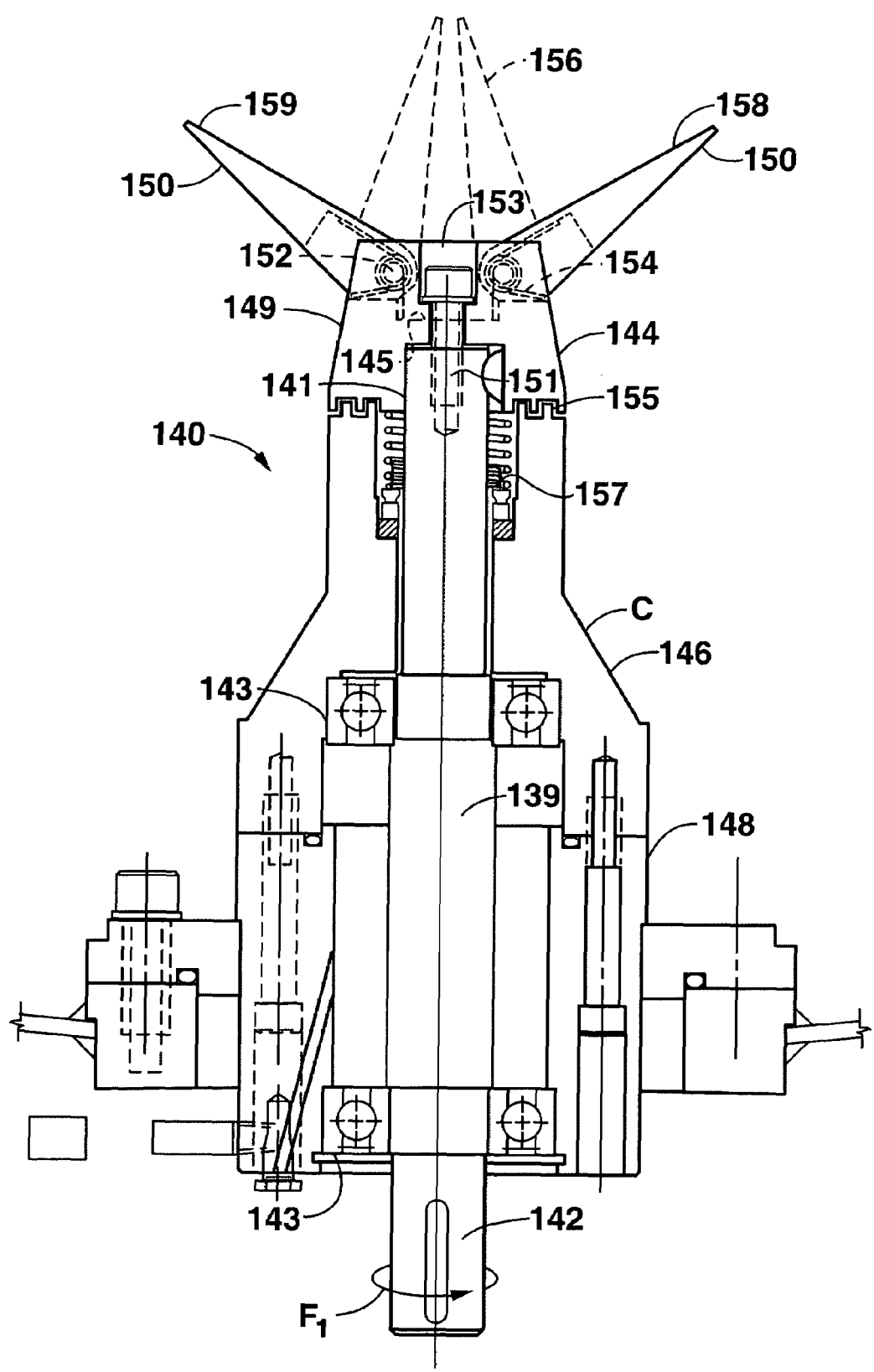
FIG. 5 is a cross-sectional view illustrating an exemplary embodiment of an agitator in accordance with the present invention.

As can be seen from FIGS. 3 and 5, the internal shaft 142 of the agitator 140 extends vertically through the bottom of the processing chamber 120 and up through a stationary lower agitator housing 148 and a stationary upper agitator housing 146. The internal shaft 142 is mounted in ball bearings 143 that permit the internal shaft 142 to rotate within the upper agitator housing 146 and the lower agitator housing 148. Due to the environment in which the agitator 140 operates, the internal shaft 142 is protected with a labyrinth seal 155 and interior seals 157 to prevent fluid from the processing chamber 120 from leaking into the bearings 143 and further, from leaking outside the processing chamber 120.

The internal shaft 142 is connected to a rotating tapered blade carrier 144. The blades 150 of the agitator 140 are affixed to the tapered blade carrier 144. The blades 150 are attached to the tapered blade carrier 144 so that the blades 150 pivot at the tapered blade carrier 144 about blade pin pivot points 152. The blades 150 are spring-loaded via torsion springs 154 so that, when not turning, the blades 150 reside in an upward resting position 156. By having the blades 150 biased upwards in a resting position when the agitator is at rest, better permits removal of the neutralized waste from the processing chamber 120.

The agitator blades 150 and the tapered blade carrier 144 are secured to the internal shaft 142 via a retaining cap 153. The retaining cap 153 can be secured to the internal shaft 142 by screwing the cap 153 into the internal shaft 142 and thereby holding the taper blade carrier 144 to the internal shaft 142 as shown in the illustrated embodiment. The retaining cap 153 may have a threaded member 151 that is inserted through an aperture 145 in the blade carrier 144. The threaded member can then be screwed into a threaded aperture 141 in the top of the internal shaft 142. It may be preferable that the retaining cap be screwed into the threaded aperture 141 in a reverse direction to the direction in which the internal shaft 142 spins. The retaining cap used in the agitator 140 may employ some other conventional method to secure the tapered blade carrier 144 to the internal shaft 142 such as an adhesive bonding or a mechanical spring latch.

To rotate the internal shaft 142 and thus the blades 150, the bottom of the internal shaft 142 is connected to a drive unit. The drive unit may be any conventionally known drive system. For example, the dive unit may be a motor that drives a belt and pulley system. In such an example, the motor may turn a belt that in turn rotates the internal shaft 142 in a direction $F_1$ as shown in FIG. 5. The internal shaft 142 may also be rotated in a direction counter to direction $F_1$.

As the motor spins the internal shaft 142, the tapered blade carrier 144 also spins, and as the tapered blade carrier spins, centrifugal force causes the agitator blades 150 to extend to an outward position 158 into the processing chamber 120. When the agitator blades 150 are fully extended, they remain tilted upward at the free ends 159 so that the ends 159 of the agitator blades 150 are higher than the blade pin pivot point 152 on the tapered blade carrier 144. These outwardly spinning agitator blades 150 cause the water in the processing chamber 120 to churn and bring the infectious waste contents of the processing chamber 120 into contact with the spinning blades 150.

Infectious waste is generally bagged in plastic bags, and as such, will be put into the processing chamber while still in the plastic bags. Much of the waste contained in the plastic bags is plastic tubing, plastic and textile bandages and wound treatment material and paper products. However, the waste often also contains syringes, lancets, and other disposable medical instruments or devices. When these bags come in contact with the spinning agitator blades 150, the agitator blades 150 rip open the bags and expose the infectious waste contents of the bags to the superheated process water in the processing chamber 120. At the same time, the fast rotating blades 150 strike the plastic tubing, paper products and plastic and textile wound treatment material, breaking and tearing this waste into small pieces and strands.

The dissevered infectious waste comprising the stringy textile material, plastic tubing and bags torn apart by the blades 150 has a tendency to wrap around the tapered blade carrier 144 and agitator blades 150. The waste tends just to wrap around the taper blade carrier 144 and not the stationary upper and agitator housings 148, 149 due to the rotation of the tapered blade carrier 144. The tapered blade carrier 144 is tapered toward the free end 149. The angle of the taper is such that the pressure generated by the wrapping of material causes the resultant force to push the material upward.

When the wrapping of waste material generates sufficient force about the tapered blade carrier 144, the wrapped waste material then pushes upward against the agitator blades 150. Since the blade pin pivot points 152 of the agitator blades 150 are lower than the blade ends 159, when the force of the wrapped material overcomes the centrifugal force that extends the agitator blades 150 into outward positions 158, the agitator blades 150 momentarily retract by pivoting about the blade pin pivot points 152 toward resting blade position 156. This momentary retraction causes the wrapped material to dislodge and sling upward and off of the agitator blades 150. As soon as the wrapped waste slings off, the agitator blades 150 again pivot to outward position 158. To facilitate the dislodging and slinging off of the wrapped material, the agitator blades 150 are also tapered from their pivot point 152 toward the free ends 159 so that the agitator blades 150 are smaller at their extreme ends.

In this manner, the waste being neutralized can be lessened in volume, while preventing the agitator 140 from being immobilized or rendered inoperable for its intended duty by the waste being neutralized. The blades 150 should be sturdy enough to withstand contact with syringes, lancets or some other hard medical devices disposed in a bag in the processing chamber 120. The flexibility provided by spring loading the blades 150 allows for the blades 150 to be deflected upward if a hard piece waste such as a disposable medical device comes in contact with one of the blades 150. Through an appropriate set-up of a control system as described above, the agitator 140 can be monitored and controlled. Any conventional suitable control system or systems may be employed.

In an exemplary embodiment, a sieve apparatus may be provided within the processing chamber to prevent the waste that has been neutralized from flow with the process water back through system. As shown in FIGS. 3, a sieve apparatus 160 is provided in the processing chamber 120. The sieve apparatus 160 is a sieve basket 162. The sieve basket 162 fits inside the processing chamber 120 and is equipped with elastomeric seals 170 to seal the sieve/processing chamber interface. The seals 170 help to contain the waste inside the sieve basket 162 and aid in preventing waste material from exiting the processing chamber 120 through the line 128. The sieve basket 162 is also preferably constructed with an opening 164 in the bottom 168 of the sieve basket 162 to permit the agitator 140 to extend through the bottom 168 of the sieve basket 162. The opening 164 has a seal 172 around the edges of the opening 164. The seal 172 interacts with the agitator 140 to prevent waste from exiting through the opening 164 during processing and when the process water is being drained through line 128.

Figure 6:
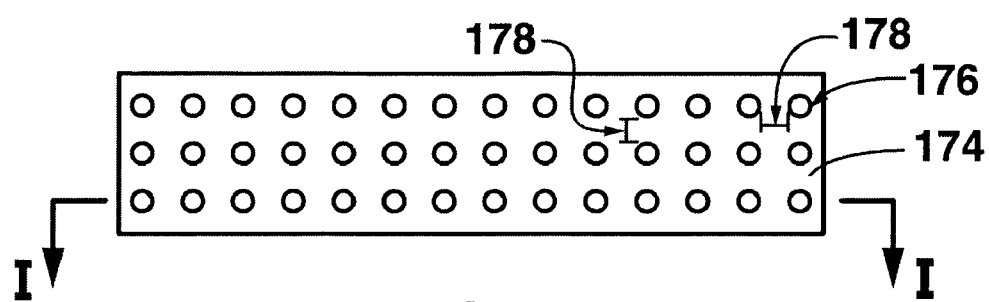
FIG. 6 is a top view illustrating a portion of a sieve in accordance with the present invention.
Figure 6A:
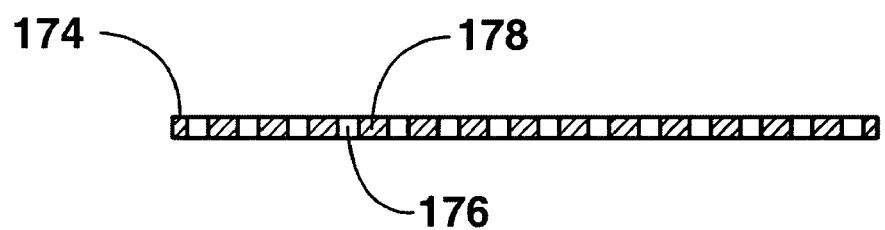
FIG. 6A is a cross-sectional view along lines I of the portion of the sieve as shown in FIG. 6.

The sieve apparatus 160 in the form of the sieve basket 162 define sieve holes 176 as shown in sieve section 174 in the FIG. 6. The sieve holes 176 allow the process water to enter through the sieve apparatus 160 so that infectious waste contained by the sieve apparatus 160 can be neutralized. Further, the sieve holes 176 permit the process water to drain from the sieve apparatus 160 while containing the waste within the sieve apparatus 160 and the processing chamber 120.

Due to the spinning of the agitator blades 150, the processed waste often includes fibrous waste material from the shredded waste. It has been found if the sieve holes are too large, the space that separates the holes catches the fibrous waste material near the middle of the waste, the ends of the fibrous waste material pass through the sieve holes and become entangled on the backside of the sieve apparatus. Once the waste becomes entangled in this manner, it is very difficult and time consuming to remove from the sieve apparatus. Once enough fibrous waste material has entangled in this manner, the flow of water will almost completely stop, adversely affecting the neutralization process time.

It is thus advantageous for the sieve holes 176 to contain the processed fibrous waste material by allowing process water to pass through the sieve, while also rendering the portion of any fibrous material that passes through the sieve holes 176 too short to become entangled on the backside of the sieve apparatus. This may be accomplished by having sieve holes 176 with an appropriate diameter and spaced at an appropriate distance 178. For example, the sieve holes 176 may have sizes from about 0.020 inch diameter to about 0.078 inch diameter that are spaced from about 0.040 inches apart to about 0.125 inches apart. In some embodiments, it may be preferable to have sieve hole sizes of 0.033 inches in diameter and spaced at distances of 0.055 inches. By employing sieve holes 176 sized at such diameters and spaced at such distances 178, fibrous waste material will lie across the inner surface of the sieve apparatus and will fall away from the sieve apparatus when the sieve apparatus is emptied.

The sieve basket 162 possesses loops 166 to aid in the loading of the waste into the processing chamber 120 and unloading of the waste from processing chamber 120. In the exemplary embodiment shown in FIGS. 2 and 3, a removal apparatus 180 is provided to load and remove the waste from the processing chamber. The removal apparatus 180 is a hoist 182 having a hooking device 186 that is extendable and retractable from a hoist arm 188. The hooking device 186 form hooking arms 184 that are insertable into the loops 166 of the sieve basket 162. Once the hooking arms are inserted into the loops 166, the sieve basket 162 can be lifted into or removed from the processing chamber 120. Due to the upward resting position 156 of the blades 150 of the agitator 140, the sieve basket 162 can easily be removed and returned to its position in the processing chamber 220 without interference from the agitator 140. The hoist arm 188 can be rotated about the hoist support 189. The hoist 182 can thereby facilitate the insertion and extraction of the sieve basket 162 before and after processing.

In this manner, the sieve basket 162 can be loaded with infectious waste and then can be inserted into the processing chamber 120, while the sieve basket 162 can then be removed from the processing chamber 120 for dumping or removal of the neutralized waste. The loading of the sieve basket 162 can be done manually or through automation. For example, the sieve basket 162 may be loaded by dumping a container carrying the infectious waste into the sieve basket 162 while the sieve basket 162 is in the processing chamber 120 or while it is outside of the processing chamber 120. After the processing of the waste, the sieve basket 162 can be removed from the processing chamber 120 by the hoist 182 and then automatically dump the neutralized waste onto a conveyor belt or into a container for disposal by inverting the sieve basket 162. In this manner, operator contact with the contents of the sieve basket 162 is eliminated. When the sieve basket 162 has been repositioned in the processing chamber 120, the processing chamber is ready for the next cycle.

Figure 4:
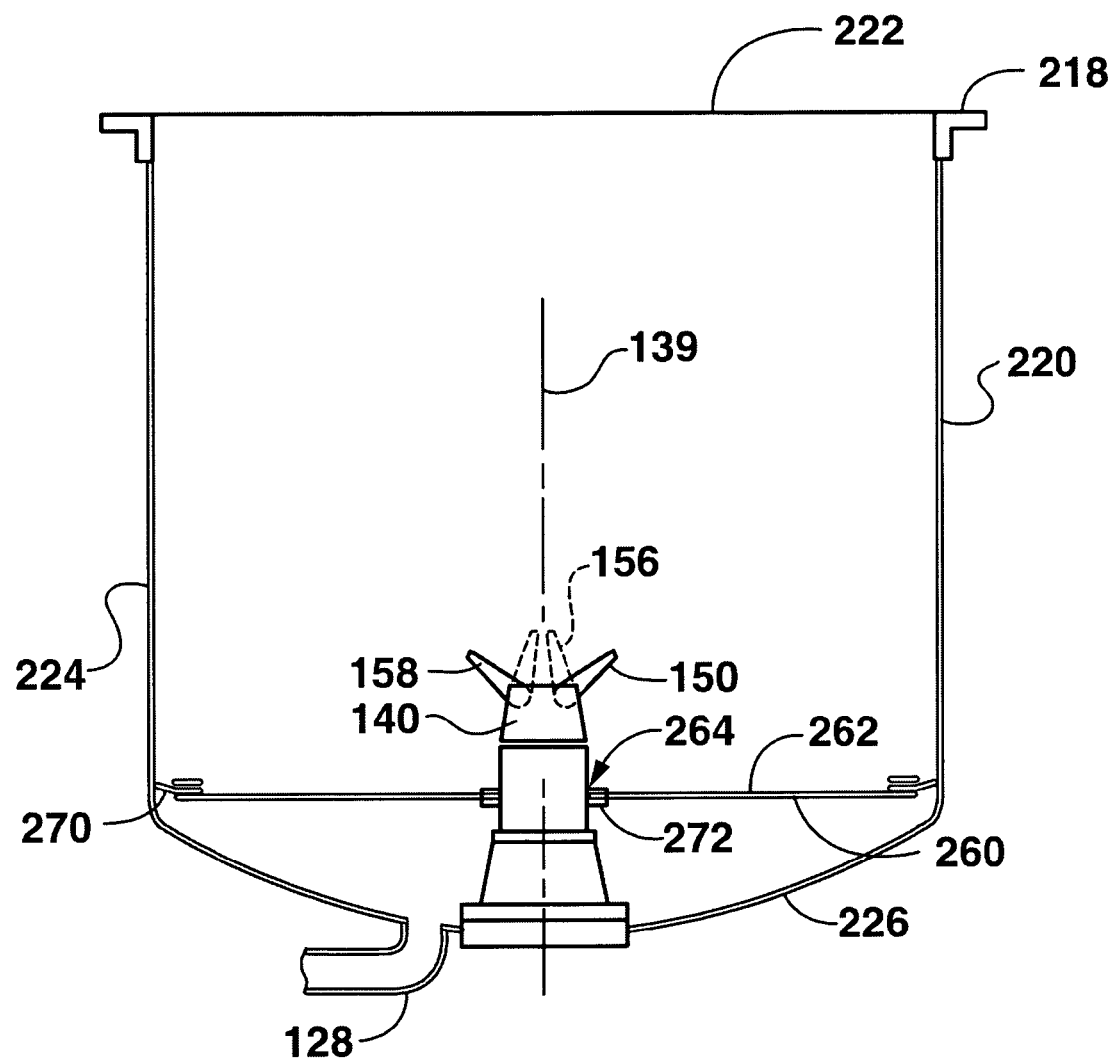
FIG. 4 is a cross-sectional view illustrating a further exemplary embodiment of a processing chamber in accordance with the present invention.

FIG. 4 shows a further embodiment of a processing chamber 220. This processing chamber 220 has a concave bottom 226 surrounded by walls 224 and employs a different sieve apparatus 260. The processing chamber 220 is equipped with an integral sieve 262 serving as the sieve apparatus 260. The integral sieve 262 is placed above the concave bottom 226 of the processing chamber 220, and is equipped with elastomeric seals 270 to seal the sieve/processing chamber interface. The exemplary integral sieve 262, as with the sieve basket described above, is constructed with an opening 264 to permit the agitator 140 to extend through the integral sieve 262. The opening 264 has a seal 272 around the edges of the opening 264. The seal 272 interacts with the agitator 140 to prevent waste from exiting through the opening 264 during processing and when the process water is being drained through line 228.

The purpose of the integral sieve 262 is the same as the sieve basket 162. The integral sieve 262 allows the process water to drain out of the processing chamber 220 while keeping the neutralized solid waste products in the processing chamber 220. However, the processing chamber 220 is unloaded in a different manner. Instead of removing the waste by removing the sieve apparatus 260, the sieve apparatus 260 remains in place while processing chamber 220 can be tilted or inverted along an axis to dump the waste contents out through the opening 222 into a desired container or onto a conveyor system to dispose of the waste.

A different removal apparatuses may be used to invert processing chambers, like processing chamber 220. The removal apparatus used to invert the processing chamber may be a manual apparatus or an automated apparatus. The removal apparatus may also incorporate a mechanism to aid in loading the processing chamber.

Figure 7B:
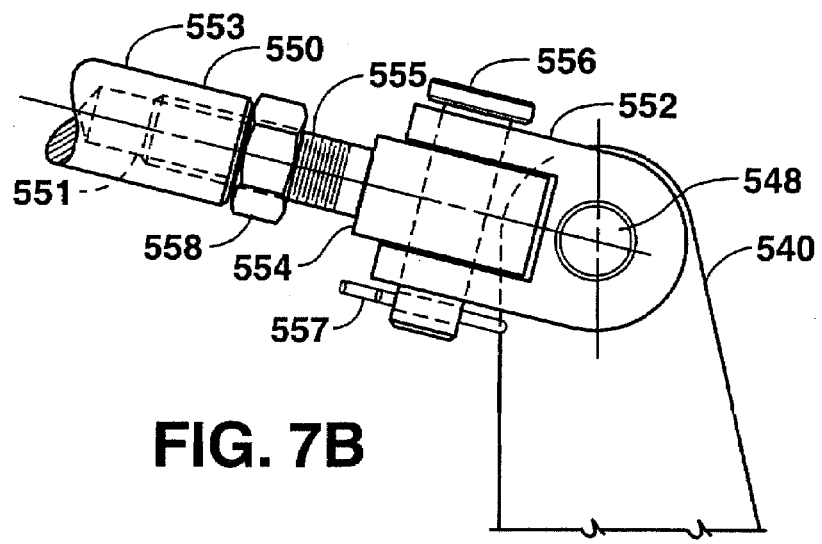
FIG. 7B is a magnified view of section II of the chamber closure member of FIG. 7.
Figure 7A:
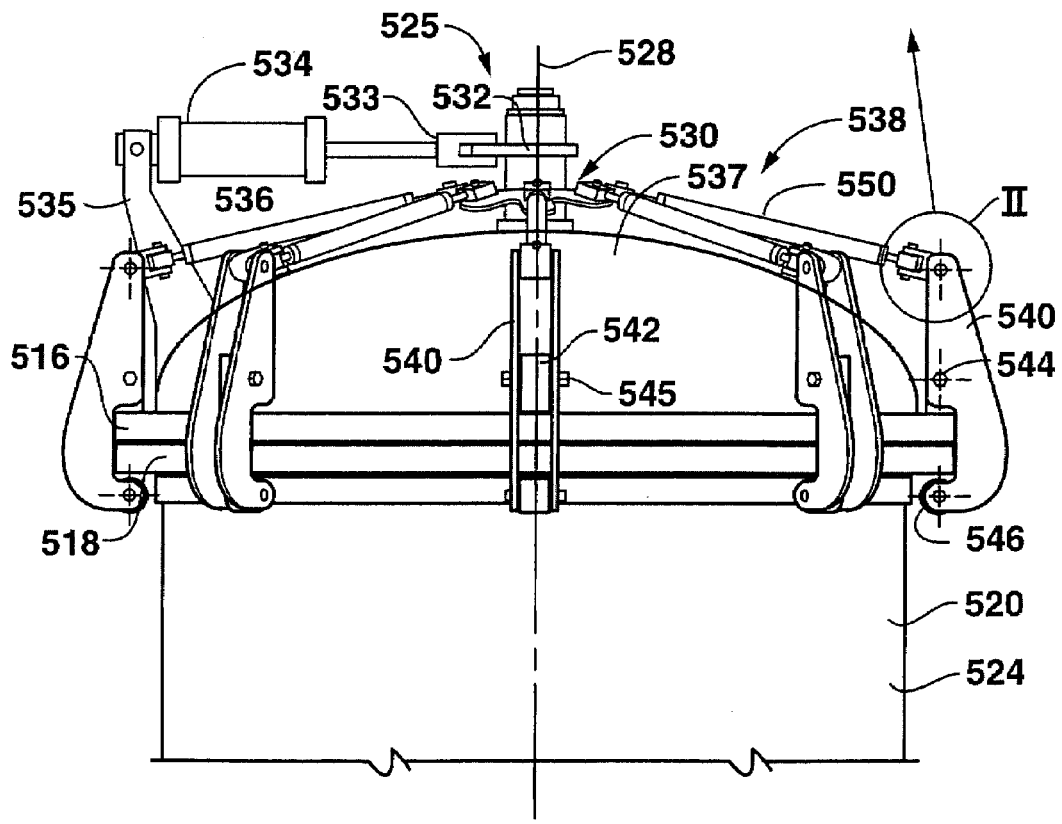
FIG. 7A is an elevation view illustrating an exemplary embodiment of a chamber closure member in accordance with the present invention.

For example, in the exemplary embodiment shown in FIG. 7, a processing chamber 320 that can be manually inverted is schematically illustrated. Such a processing chamber would be a small processing chamber used in doctor offices, clinics, or other places where a minimal amount of medical/bio waste is created on a daily basis. The processing chamber 320 is attached to a removal apparatus 380. The removal apparatus 380 in the form of a rotation unit 382 includes chamber supports 325 on either side of the processing chamber 320 with each support 325 having an aperture through which a rotating member 332. The rotating members 332 are secured to the processing chamber 320 and rotate on within the supports 325 about an axis 386.

The process water supply line and the steam supply line (not shown) pass through the rotating member 332 through the use of rotary couplings as shown in FIG. 1. The pipes that extend outward from the rotating members 332 on the rotating member side of the rotary couplings and feed the steam and process water to the processing chamber 320 rotate with the processing chamber 320. In this manner, the process water and steam can be fed into the processing chamber 320 from the bottom, while still permitting the processing chamber to rotate about the axis 386. At least one handle 384 is connected to at least one rotating member 332 to allow rotation of the processing chamber 320 to an inverted position 320'.

To process the waste, a closure member 338 is positioned in an open position 338' and the waste to be treated is placed in the processing chamber 320 on top of an integral sieve as described above. The closure member 338 is then placed in a closed position along a rim 318 of the process chamber 320. The process water and steam, as needed, pass through the water and steam supply lines into the processing chamber 320. An agitator as described above thoroughly mixes the process water and the waste thereby neutralizing the waste.

Once the waste in neutralized and the process water is drained from the processing chamber 320, the closure member is reopened to the position 338'. The handles 384 can then be used to rotate the processing chamber 320 into an inverted position 320' to dump the neutralized waste into a container 330 for disposal. After the waste is removed from the processing chamber 320 in this manner, it may be rotated back to the processing position to start the process again.

In this manner, a light weight processing chamber which uses less superheated process water and processes less waste can be manually loaded and unloaded. A system employing the processing chamber 380 allows an expensive alternative to larger system which require mechanical assisted or automated loading and unloading for institutions that create a limited amount of bio waste. Other manual features of this smaller machine may include the manual opening and closing of the closure member 338.

Figure 11A:
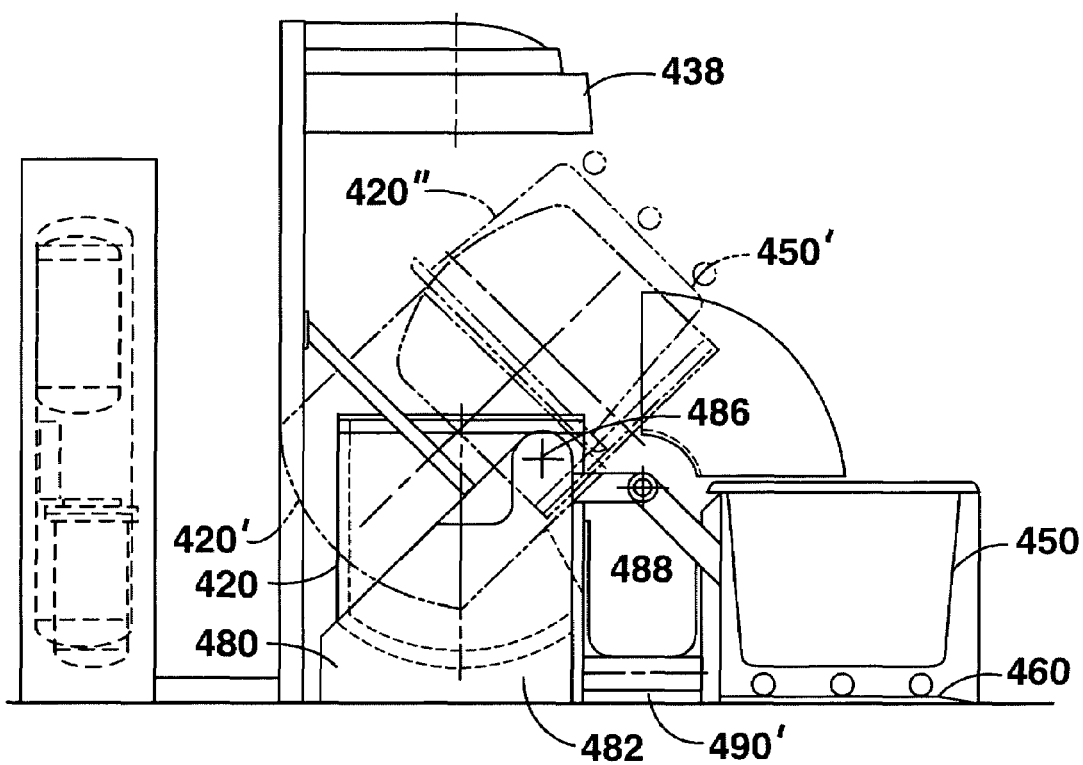
FIG. 11A is a schematic side view illustrating another exemplary embodiment of a processing chamber and removal apparatus in accordance with the present invention.

In a different exemplary embodiment, as shown in FIGS. 11A and 11B, a processing chamber 420 may be loaded and unloaded automatically. Such processing chamber 420 can be employed in larger institutions such as hospitals, which create a large amount of medical and bio waste on a daily basis. The processing chamber 420 is positioned in and operably connected to a removal apparatus 480. The removal apparatus 480 is an automated rotation unit 482 that mechanically rotates the processing chamber 420 about an axis 486. For example, the rotation unit may employ a hydraulic system to rotate the processing chamber 420. As with the manual inverting removal apparatus described above, the process water supply line and the steam supply line (not shown) are connected to the process water pipe and steam pipe (not shown) that feed into the processing chamber 420 by rotary couplings to allow the process water pipe and steam pipe to rotate with the processing chamber 420.

To process the waste in the processing chamber 420, a container, or bin, 450 containing bagged infectious waste is placed on a scales platform 460 and weighed to determined the amount of bagged infectious waste to be placed in the processing chamber 420. Upon the determination of the weight of the waste, a delivery arm 488 lifts the container 450 from the scale platform 460 in front of the processing chamber 420 and rotates it toward the processing chamber 420. At the same time or at some point earlier, the rotation unit 482 rotates the processing chamber from a processing position to a receiving position 420'. The delivery arm 488 rotates the container 450 to a dumping position 450' where the waste contents within the container 450 are dumped into the processing chamber 420 in the receiving position 420'. To facilitate loading, a rotation unit 482 is capable of rotating the processing chamber 520 45° to the receiving position 420', and rotating the container 450 135° to the dumping position 450' to load the contents of the container 450 into the processing chamber 520.

Once the delivery arm 488 returns the container 450 back to the scales platform 460 and the processing chamber 420 is rotated back to the upright processing position, a closure member 438 is lowered into a closed position against the process chamber 420. The process water and steam, as needed, pass through the water and steam supply lines and pipes into the processing chamber 420. An agitator 440 is rotated by a drive unit 441 to thoroughly mix the process water and the waste thereby neutralizing the waste. As with the process water and steam pipes, the drive unit 441 rotates with the processing chamber 420 about the axis 486.

Once the waste in neutralized, the process water is drained from the processing chamber 420 while an integral sieve as described above retains the processed waste within the processing chamber 420. The closure member 438 can then be reopened. The closure member should be raised far enough above the processing chamber 420 to allow the rotation unit 482 to rotate the processing chamber 420 to an ejection position 420". In this position 420", the waste is dumped from the processing chamber 420 onto a conveyor belt 492 of a conveyor system 490. The conveyor system 490 was walls 494 to help keep the waste on the conveyor belt. The waste material is then carried by the conveyor system 490 to an on-site shredder and/or compactor before being removed from the facility.

Through an appropriate set-up of a control system as described above, the removal apparatus 180, 380, 480 can be monitored and controlled. Any conventional suitable control system or systems may be employed.

The processing chambers are equipped with a chamber closure members, or tops, that hermetically seal the unobstructed openings in the processing chambers to allow pressure to build within the processing chambers without allowing the pressure to escape. These closure members can be of different construction, depending on the size and type of processing chambers. Further, different types of latching systems may be used to secure the closure member to the processing chamber.

FIGS. 7, 7B, 8A, 8B, 9A and 9B illustrate an exemplary embodiment of a closure member 538 which is used to seal the processing chamber 520. The closure member 538 includes a lid 537 is lowered onto the processing chamber 520 and secured into position against a chamber flange 518 of the processing chamber 520 by a latching system 525 positioned on the lid 537. In the exemplary embodiment, the latching system 525 includes a rotatable multi-fingered hub 530 connected to latch arms 540 by connecting rods 550. The multi-fingered hub 530 may be rotated in a first direction to cause the latch arms 540 to secure the closure member 538 to the processing chamber 520 and may be rotated in a second direction to release the latch arms 540 and the closure member from the processing chamber 520.

The multi-fingered hub 530 is centrally located on the lid 537 of the closure member 538. The lid 537 of the closure member 538 has a rim 516 around its lower edge which is contactable with the chamber flange 518 around the opening at the top of the walls 524 of the processing chamber 520. The rim 516 has mounting brackets 542 mounted thereto. Each of the latch arms 540 is pivotally connected to a corresponding mounting bracket 542 by a pivot pin 545, which is positioned through alignable apertures in both the mounting brackets and the latch arms 540.

A connecting rod is run between the multi-fingered hub 538 and each latch arm 540. At one end of the connecting rods 550 as shown in FIGS. 8A and 8B, the connecting rods 550 each include a rod body 553, a ball rod end 562 and a rod end 554. Each connecting rod 550 is attached to the multi-fingered hub 530 by a corresponding ball rod end 562 with a bolt 563 and nut 561. Each finger 529 of the multi-fingered hub 530 defines a receiving aperture 531 through which the bolt 563 of the ball rod end 562 passes. The nut 561 is tightened onto the bolt 563 of the ball rod end 562 on the opposite side of the finger 529 of the multi-fingered hub 530. The ball rod end 562 is rotatable about the bolt 563.

At the opposing end of the connecting rods 550 as shown FIGS. 7B, 8A, and 8B, the connecting rods 550 are attached to the latch arms 540 by a rod ends 554. The rod ends 554 are connected to a swivel brackets, or clevises, 552 by pins 556 that are secured by cotter pins 557. The swivel brackets 552 allow the rod ends 554 to rotate about the pins 556. Each swivel bracket 552 is, in turn, connected to a corresponding latch arm 540 by a pin 548. The body 553 of each connecting rod 550 has a threaded hole 551, 568 at each end 558, 566. The rod ends 554 have right-handed threads 555 which allow the rod ends 554 to be screwable into the threaded holes 551 at the latch end 558 of the body 553 of the connecting rods 550. Conversely, the ball rod ends 562 have left-handed threads 564, which allow the ball rod ends 562 to be screwable into the threaded holes 568 at the hub end 566 of the body 553 of the connecting rods 550. In this manner, the length of the connecting rods 550 can be adjusted. In particular, by rotating the body 553 in one direction or the other, the connecting rod 550 may be lengthened or shortened due to the orientation of the threads 555, 564 on the respective ball rod end 563 and rod end 554. Other conventional methods and configurations may also be used to make the lengths of the connecting rods 550 adjustable.

Different drive mechanisms can be used to rotate the multi-fingered hub 525, for example a hydraulic drive system. In the exemplary embodiment, a hydraulic cylinder 534, which is operated in a conventional manner by a hydraulic system, is attached to a support arm 535 to stabilize the cylinder 534. The piston arm 536 of the cylinder 534 with a cylinder bracket 533 on its free end is connected to a hub lever 532 by the cylinder bracket 533. The hub lever 532 is attached to the multi-fingered hub 530.

Figure 9A:
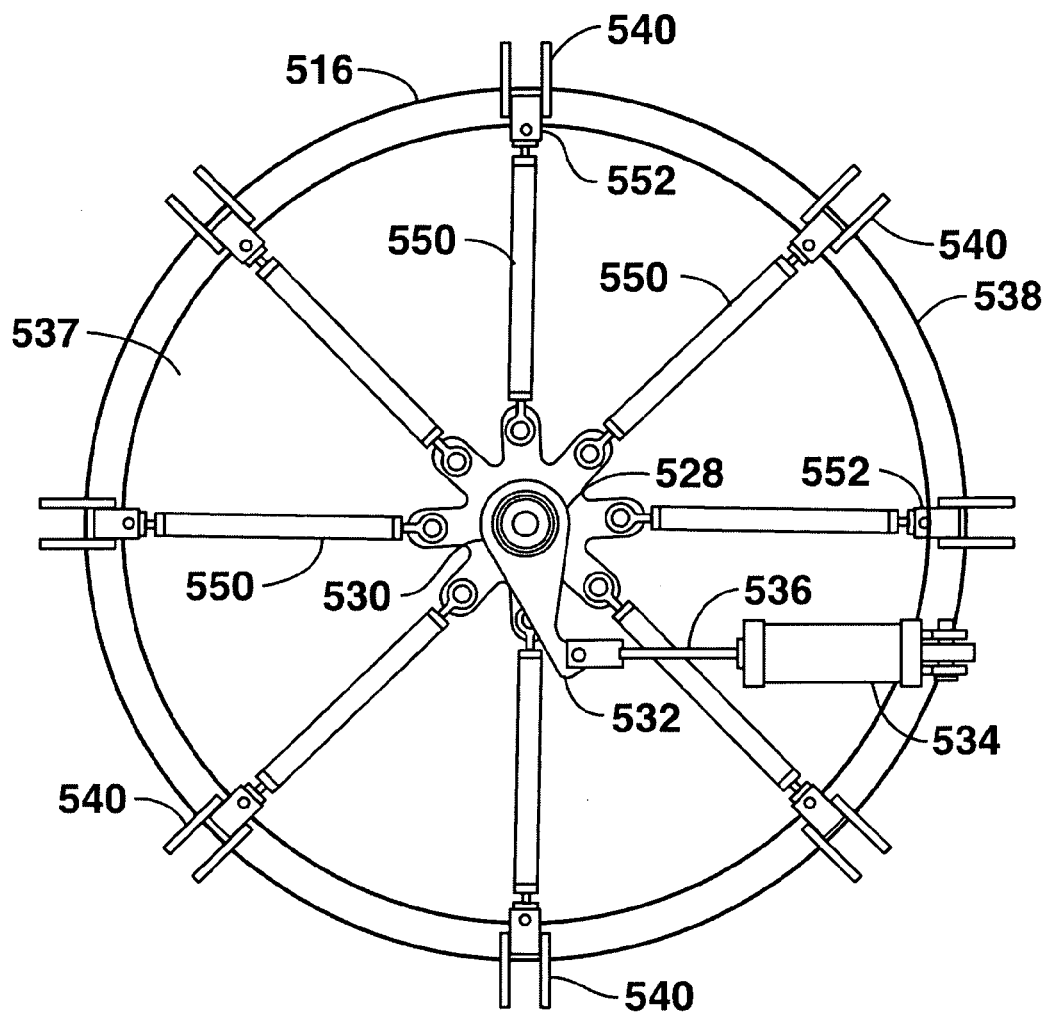
FIG. 9A is a top view of the chamber closure member of FIG. 7 with the latch arms in a closed position.

When the piston arm 536 of the cylinder 534 is in a retracted position as shown in FIGS. 7 and 9A, the closure member 538 is in a closed and sealed position against the chamber flanges 518 of the processing chamber 520. In the closed position, each of the connecting rods is in an aligned position 550' in line with the corresponding latch arm 540. The latch arms 540 have been rotated about the mounting brackets 542 at the axes 544 so that rollers 546 held at the ends of the latch arms 540 distal from the end carrying the swivel bracket 552 reside under the chamber flange 518 of the processing chamber 520.

Figure 9B:
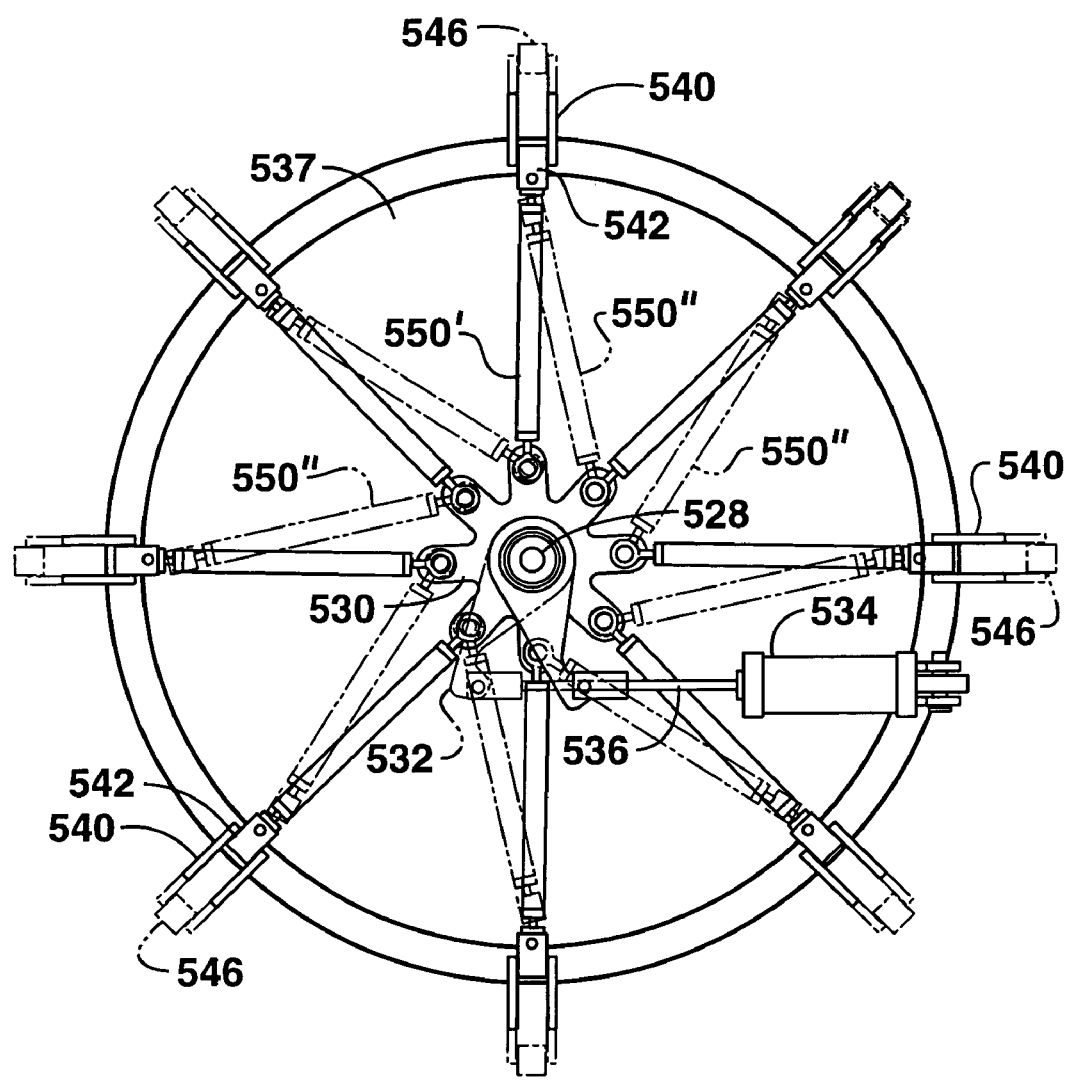
FIG. 9B is a top view of the chamber closure member of FIG. 7 with the latch arms in an opened position.
Figure 10:
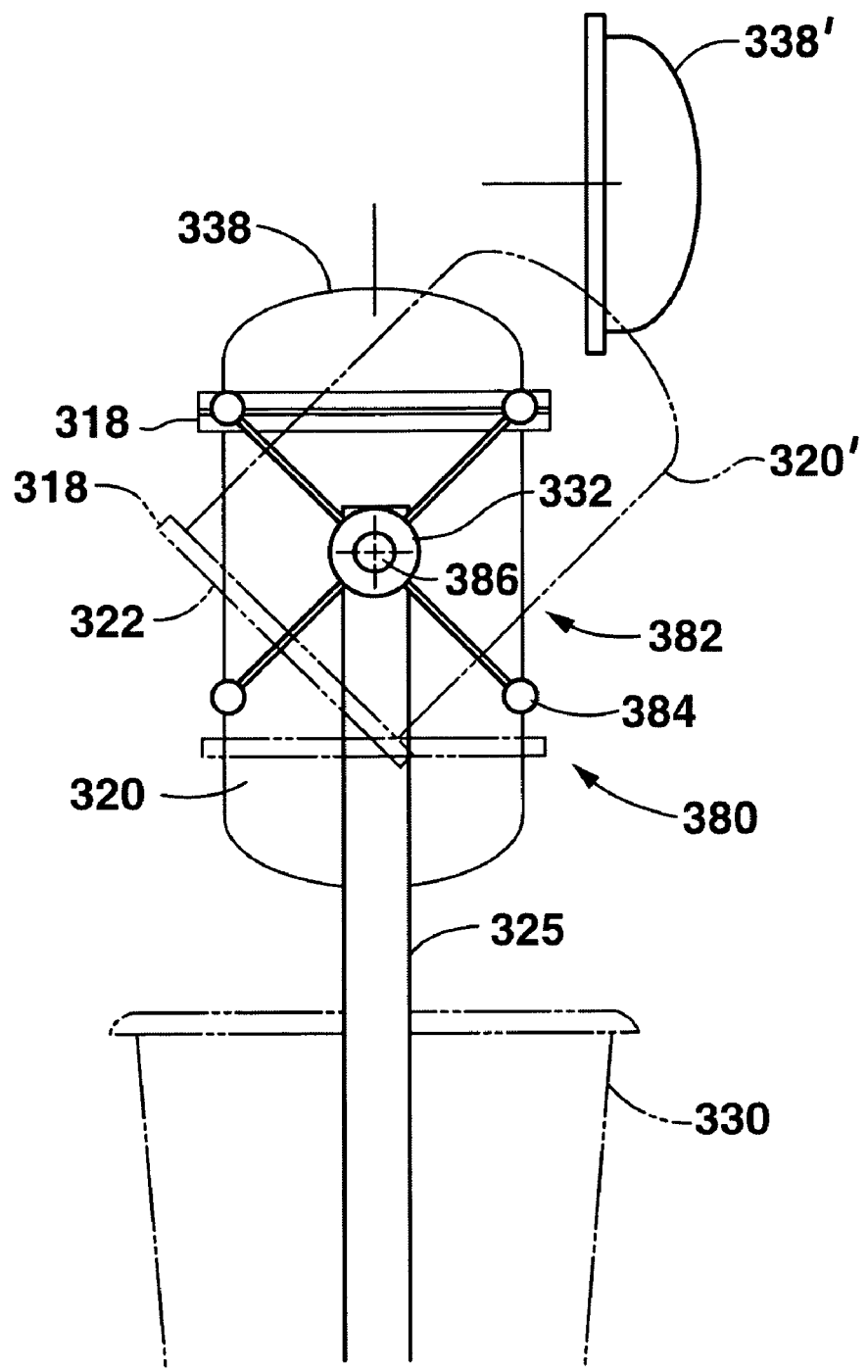
FIG. 10 is a schematic side view illustrating an exemplary embodiment of a processing chamber and removal apparatus in accordance with the present invention.

As the piston arm 536 is extended from the cylinder, the hub lever 532 rotates the hub 530 about the hub axis 528 in a direction $V_1$. The rotating hub 530 pulls the connecting rods 550 in the direction the hub 530 is rotating. As the connecting rods 550 are pulled, the swivel brackets 552 pull on the latch arms 540 causing them to rotate upward about the mounting brackets at the axes 544. In this manner, the rollers 546 dislodge from under the chamber flange 518 and the latch arms 540 are raised as shown in FIG. 9B. The closure member 538 can then be lifted from the processing chamber 520.

In the opened position of the closure member 538 as shown in FIG. 9B, each of the connecting rods are in a slanted position 550" in line with the corresponding latch arm 540. The latch arms 540 have been rotated about the mounting brackets 542 at the axes 544 so that the end of the latch arms 554 carrying the rollers 546 are extended in an outward position.

Once the processing chamber 520 is loaded again and it is ready to be closed, the closure member 538 is placed in a closed position and the latch system 525 is activated again. As the piston arm 536 is retracted back into the cylinder 534, the hub lever 532 rotates the hub 530 in a direction $V_2$. The connecting rods 550 are pushed from the slanting position 550" to the aligned position 550'. As the connecting rods 550 are pushed, the swivel brackets 552 push the latch arms 540 causing them to rotate downward about the mounting brackets at the axes 544. In this manner, the rollers 546 roll under the chamber flange 518 and the latch arms 540 are placed in a closed position as shown in FIGS. 7 and 9A.

A seal is carried in the closure member 538 that interacts with the processing chamber 520 to ensure the pressurized closing of the processing chamber 520. The seal can be designed to increase its sealing effective as the pressure builds in the processing chamber 520. In such a manner, the closure member 538 and latching system 525 can hermetically seal the processing chamber 520.

The chamber flange 518 may define a slightly raised portion on the bottom of chamber flange 518. As the rollers 546 on the latch arms 540 move under the chamber flange 518 on the processing chamber 520, the rollers 546 travel over the slight raised portion on the bottom of the chamber flange 58. As pressure builds in the processing chamber 520, the closure member 538 is pushed upward by the pressure, which makes it more difficult for the rollers 56 to travel back over the raised portion on the bottom of the chamber flange 518. The sealing member that prevents leakage between the processing chamber 520 and the closure member 538 may be a lip type, with the lip pointed inward so that as pressure builds in the processing chamber 520, the pressure on the seal exerts more force on the chamber flange 518. Such a construction also allows for a slight upward movement of the closure member 538 without causing a leak and locks the rollers 546 on the latch arm 540 in place.

The number of latch arms 540 used in the latch system 525 may vary. However, it is preferable that at least two latch arms are employed to facilitate sealing of the closure member 538 to the processing chamber 520.

The latching system 525 creates an "over-the-center" type fastening between the closure member 538 and the processing chamber 520. The aligning of the fingers 529 of the hub 530, the connecting rods 550 and the latch arms 554 when the connecting rods are in the aligned position 550' in the closed position of the latching system 525 creates a more stable fastening of the closure member 538 to the processing chamber 520. Simultaneously, the alignment of each of the latch arms 554 so that the corresponding swivel brackets 552, axes 544 and the rollers 546 are at least proximally in a straight line also creates a more stable fastening of the closure member 538 to the processing chamber 520.

Through an appropriate set-up of a control system as described above, the closure member 38, 138, 338 438, 538 and/or latch system 525 can be monitored and controlled. Any conventional suitable control system or systems may be employed.

It would be appreciated by those skilled in the art that various modifications and variations can be made in the present invention without departing from the scope of the invention. It is intended that the present invention include such modifications and variations as come within the scope of the appending claims and their equivalents.

What is claimed is:

1. A system for processing infectious waste to neutralize the waste, said system comprising:

a processing chamber for receiving infectious waste and processing water with said processing water being at an elevated temperature sufficient to process said infectious waste, said processing chamber forming an opening through which to receive and remove said waste;

a closure member carried adjacent to said processing chamber, said closure member positionable over said opening formed in said processing chamber so as to seal the processing chamber closed and removable from said opening of said processing chamber to permit receipt of said waste and removal of said waste after said waste has been neutralized;

a holding tank connected to said processing chamber, said holding tank supplying said processing water at said elevated temperature sufficient to process said infectious waste to said processing chamber; and a filter disposed between said processing chamber and said holding tank, said filter filtering said processing water that exits said processing chamber and supplying at least a portion of said filtered processing water back to said holding tank to be reused in the processing chamber.

2. A system as in claim 1, further comprising an agitator extending within said processing chamber, said agitator contactable with said waste and processing water.

3. A system as in claim 2, wherein said agitator comprises a rotatable internal shaft, said internal shaft having an axis extends through a process chamber.

4. A system as in claim 3, wherein a tapered blade carrier is connected to a first end of said shaft, said blade carrier having a plurality of blades pivoted about pivot points on said tapered blade carrier.

5. A system as in claim 4, wherein said blades in a resting position are biased upward about parallel to said axis of said internal shaft and, upon rotation of said shaft, centrifugal force causes said blades to extend from said blade carrier about said pivot points into outward positions as measured from said axis of said internal shaft.

6. A system as in claim 5, wherein a plurality of torsion springs operably connects said blades to said blade carrier to permit said blades to sling said waste that wraps around said tapered blade carrier off of said tapered blade carrier and said blades, said wrapped waste is forced upward where said waste moves said blades upwardly overcoming said centrifugal force normally biasing said blades outwardly, causing said blades to sling off said waste, said blades returning to their outward centrifugal forced bias after being freed of said waste.

7. A system as in claim 2, further comprising a sieve apparatus disposed within said processing chamber, said sieve apparatus containing the waste while within said processing chamber and facilitating drainage of said processing water.

8. A system as in claim 7, wherein said sieve apparatus comprises an integral sieve that is positioned in a bottom portion of said processing chamber.

9. A system as in claim 8, wherein said processing chamber is rotatable about an axis to facilitate the delivery and removal of said waste into and from said processing chamber.

10. A system as in claim 9, wherein upon rotation of said processing chamber, said processing chamber discards said waste onto a conveyor.

11. A system as in claim 9, wherein a delivery arm is disposed beside said processing chamber, said delivery arm moveable in a manner that allows said delivery arm to pick up containers holding said infectious waste to dump said containers into said processing chamber.

12. A system as in claim 7, wherein said sieve apparatus comprises a removable basket constructed to be received by said processing chamber.

13. A system as in claim 12, wherein said removable basket has a seal around a top of said basket to retain said waste in said basket.

14. A system as in claim 13, wherein said removable basket has an aperture in a bottom portion of said basket so that, when said basket is placed into said processing chamber, said agitator extends through said aperture in said bottom portion of said basket.

15. A system as in claim 14, wherein said aperture in said bottom portion of said basket is constructed to sealably receive said agitator.

16. A system as in claim 12, further comprising a removal apparatus disposed above said opening of said processing chamber, said removal apparatus lifting said basket from said processing chamber.

17. A system as in claim 16, wherein said removal apparatus comprises a hoist.

18. A system as in claim 7, wherein said sieve apparatus defines holes having a diameter of about 0.020 inch to about 0.078 inch.

19. A system as in claim 7, wherein said sieve apparatus defines holes spaced about 0.040 inches apart to about 0.125 inches apart.

20. A system as in claim 7, wherein said sieve apparatus defines holes that are about 0.033 inches in diameter at a spacing of about 0.055 inches apart.

21. A system as in claim 1, wherein said closure member is lowered onto said processing chamber and latched into position by means of a plurality of latch arms.

22. A system as in claim 21, wherein a first end of each of said latch arms is connected to a rotatable hub carried on said closure member, when said hub is rotated in a first direction said latch arms rotate causing a second end of each of said latch arms to latch said closure member onto said processing chamber, and when said hub is rotated in a second direction said latch arms rotate causing said second end of each of said latch arms to unlatch said closure member from said processing chamber.

23. A system as in claim 22, wherein connecting rods are operably disposed between said latch arms and hub.

24. A system as in claim 23, wherein a hydraulic cylinder rotates said rotating hub.

25. A system as in claim 23, wherein said second end of each of said latch arm has a roller that is moveable under a chamber flange on said processing chamber.

26. A system as in claim 25, wherein the movement of said latch arms causes said rollers to travel slightly past a pivot point on said latch arm, thus locking said closure member into place.

27. A system as in claim 25, wherein said hub comprises a multi-fingered hub.

28. A system as in claim 1, further comprising a transfer tank disposed between said filter and said holding tank, at least a first portion of said process water passing through said transfer tank from said filter to said holding tank under pressure with a second portion of said process water being retained in said transfer tank.

29. A system as in claim 28, further comprising a heat exchanger having two adjacent sides with a first side of said two sides operably connected to said transfer tank and a second side of said two sides operably connected to said holding tank, whereby said second portion of said process water from said transfer tank is drained through said first side of said heat exchanger and new process water being supplied to said holding tank is run through said second side of said heat exchanger so that said second portion of said process water transfers heat to said new process water.

30. A system as in claim 28, wherein said waste in said processing chamber is cooled after the process water is drained from said processing chamber by a supply of water.

31. A system as in claim 28, wherein said filter is connectable to a supply of water to flush said filter on a periodic basis.

* * * * *